United States Patent [19]
Goode

[11] Patent Number: 5,733,121
[45] Date of Patent: Mar. 31, 1998

[54] MANDIBLE LOCK DEVICE

[76] Inventor: MacDonald H. Goode, P.O. Box 172, Southfield, Mich. 48037

[21] Appl. No.: 827,947

[22] Filed: May 1, 1997

[51] Int. Cl.[6] ..................................................... A61C 5/00
[52] U.S. Cl. ............................................. 433/140; 600/238
[58] Field of Search .................................. 433/136, 138, 433/140; 600/238, 239, 243, 244

[56] References Cited

U.S. PATENT DOCUMENTS

| | | | |
|---|---|---|---|
| 390,561 | 10/1888 | Brown | 433/140 X |
| 841,590 | 1/1907 | Sklar | 600/244 |
| 1,137,585 | 4/1915 | Craig, Jr. | 433/140 |
| 1,598,608 | 9/1926 | Hammond | 600/239 |
| 1,813,650 | 7/1931 | Whitlock | 433/140 X |

*Primary Examiner*—Nicholas D. Lucchesi
*Attorney, Agent, or Firm*—Robert A. Spray, Patent Attorney

[57] ABSTRACT

A lock device for holding "open" position of a person's mandible (lower) jaw bone, for facilitating medical treatments such as emergency intubation and other procedures, dental work, etc., particularly on a patient who is either unconscious or for some other reason is not cooperative.

A pair of force lugs, carried on support-beam members, are for imposing a force oppositely against a person's mandible teeth set and upper or skull (maxilla) teeth set. The beam members are pivotally interconnected; and have an extension arm outwardly and rearwardly extending from the outer end, being a retroflex member which in use of the device extends generally horizontally and rearwardly along the person's cheek, providing ease of manual grasping and other advantages.

6 Claims, 6 Drawing Sheets

MANDIBLE LOCK DEVICE

I. FIELD AND BACKGROUND OF THE INVENTION

The present invention relates to medical apparatus, and apparatus for dentistry and other medical procedures, and more particularly to medical apparatus advantageously useful in holding a person's mandible (lower jaw) bone and mandible teeth in an "open" position, such as providing access to a person's throat when for some reason a rearward (flexion) condition of the person's neck would be desired but is unobtainable, and similar uses.

Although ordinarily a patient would expectedly be cooperative in adhering to the instructions of a medical professional, in certain dental procedures, respiratory, and other conditions it is very desirable and often critical to force the mandible jaw to be "locked" open, and hold it locked open.

For example, a lock-open jaw condition desirably facilitates treatments such as any including the suctioning of secretions, saliva, blood and/or other body fluids.

Suctioning may be of blood, vomitus or secretions from the oral cavity, thereby preventing these contents from aspirating into the lung fields.

A person can "drown in his own body fluids" is an expression which is sadly often true.

A keeping of the respiratory passageway open during a procedure of intubation is very desirable; yet the very condition which causes the presence of such secretions can also be the same condition which renders the patient uncooperative.

Endotracheal intubation is the passage of a plastic tube into the trachea for the purpose of ventilating a patient whose own spontaneous respiratory drive is insufficient and incompatible with life. Endotracheal intubation is a routine procedure prior to all surgical procedures which require full body anesthetics, as opposed to local, and intubation is an important use of this device.

Jaw lock devices are useful also in any digital procedure of exploration, or to free a person's tongue, and for the installation of a breather tube past the person's trachea.

Stomach pumping and exploration by lighted tube also illustrate the wide field of use, which includes many particular dental procedures, emergency care of a person who has suffered a major trauma, head injury, drug overdose, etc.

A typical use is also a sublingual injection of medication, i.e., in prehospital and/or emergency room medicine it is necessary in some cases to administer medication into the network of veins under the tongue for rapid absorption. This route is considered much faster than intramuscular injection and subcutaneous injection. Sublingual injection may be useful in cases of narcotic overdoses in which narcotic antigonists may be given to intravenous drug abusers having destroyed their peripheral vasculature from repeated intravenous injection.

Also, in cases of severe anaphylactic (allergic) reactions in which peripheral vascular collapse prevents the establishment of an intravenous lifeline for the administration of epinephrine, the device may be used to secure access to the oral cavity.

Sublingual injection is also an option for a patient whose airway is compromised by laryngeal edema, and is in near or full respiratory failure secondary to anaphylaxis.

In dental work and/or oral surgery, the device may be used in cases where the voluntary opening of the mandible is not possible. Examples of this include uncooperative children or adults, a procedure requiring an extended length of time or a patient who is fully anesthetized.

II. PROBLEMS INHERENT IN THE USE OF MANDIBLE LOCK DEVICES

The wide scope of medical procedures which utilize mandible-lock devices is obvious from the above illustrations; for although the listing is not intended to be fully comprehensive, it does indicate a variety of conditions in which one or another type mandible locks are desired.

And although each type has certain advantages, each type has certain disadvantages or limitations. For example, one of the simplest types of jaw-lock devices is a simple blocking body which the medical professional shoves between a person's sets of teeth. Such a device is considered quite economical, but, unless a great variety of sizes and/or shapes are available, the blocking body will often be bothersome, especially to digital manipulation; and to minimize chance of being swallowed, the blocking body used will inherently have a relatively large and bothersome size.

Such prior art "blocking bodies" are commercially available, being resilient bodies about 1 cm. thick, advertised as "Mouth Props" in the commercial catalog of the Meer Company, as being obtainable in four sizes each having identification numbers and manufacturers noted as follows: McKesson Large Adult, 180432, MP58; Markel Adult, 210587, MP54; Markel Child, 139122, MP52; and Markel Small Child, 310131, MP48.

Metal lock devices avoid some of the size and other problems inherent with the block body types, but they are considered relatively expensive and their component parts pose a bother especially to digital manipulation, because for the handles to be big enough to give a good "leverage force-effect", the outer ends of the handles provide a sort of barrier against the ease of access into the person's mouth.

Such metal lock devices, identified as "Mouth Gags" are advertised in the same Meer Catalog, as obtainable in two sizes, both of the Molt type, as follows: Molt Adult, 308439, MGA and Molt Child, 184454, MGC.

As a short summary of the inherent problems with prior art jaw-blockers, it might be said that the avoidance of certain characteristics of one type seem to invoke similar or other characteristics which are undesirable.

III. SUMMARY OF THE PRESENT INVENTION

A lock device for holding "open" position of a person's mandible jaw bone, for facilitating dental work and other medical treatments or intubation procedures, particularly on a patient who is either unconscious or for some other reason is not cooperative.

As with prior art mandible lock devices of Molt type, the device has a pair of force lugs for imposing a force oppositely against a person's mandible teeth set and skull teeth set.

The force lugs are carried on support-beam members which are pivotally interconnected, being generally similar to the force lugs and handle beams of a conventional pair of pliers; and a lock feature acts between the handle beams to hold the lugs forcefully open.

Departing significantly from the prior art, the handle beams of this mandible lock device each have an extension arm outwardly and rearwardly extending from the outer end, being a retroflex portion which in use of the device extends generally horizontally and rearwardly along the person's cheek, providing ease of manual grasping and other advantages with minimal obstruction of manipulation.

The exterior-laterally placed handles protect the patient from airway blockage and/or stimulation of the vagus nerve coughing/gag reflex; and stimulation of the vagus nerve can cause lethal cardiac dysrhythmias including bradycardia and asystole, should the jaw-lock device become dislodged from between the patient's teethset.

The construction also accommodate manufacture by disposable plastic material which reduces the cost of each individual unit and prevents the transmission of diseases.

IV. PRIOR ART CAPABILITY AND MOTIVATIONS, AS HELPING TO SHOW PATENTABILITY HERE

Even in hindsight consideration of the present invention to determine its inventive and novel nature, it is not only conceded but emphasized that the prior art had many details usable in this invention, details of both capability and motivation, but only if the prior art had had the guidance of the present concepts of the present invention.

That is, it is emphasized that the prior art had/or knew several particulars which individually and accumulatively show the non-obviousness of this combination invention. E.g.:

(a) The prior art has had pliers-type devices of Molt type for mandible locking for many years, even those with pivotal handles for use by spreading the handles in contrast to the usual closure of handles as most pliers operations use;

(b) The prior art has long realized the disadvantages of known type of mandible locks, for not only a dental use but for various other uses of an intubation and other medical procedures;

(c) It seems likely that many if not most users and manufacturers of medical apparatus, particularly of mandible lock devices, would have realized the need to provide an advantageous and novel mandible lock device, having ease of installation and adjustment, but without obstructing the mouth region and mouth access unduly;

(d) The ease of tooling for the present invention has surely given manufacturers ample incentive to have made modifications for commercial competitiveness in a competitive industry, if the concepts had been obvious;

(e) The features of the present invention are reasonably likely considered by manufacturers and users to be of such an obvious advantage to medical professionals that manufacturers and/or users would likely consider devices of this invention to have massive sales opportunities to a great multitude of medical professionals; and thus manufacturers and/or users would have been likely to have developed this article if its concepts had been obvious;

(f) The disadvantages of prior art mandible lock devices have been of such a likely actual and universal nuisance, personally to a large number of users, that surely one would have created this invention if the concepts had been obvious;

(g) The prior art has always had sufficient skill to make many types of mandible jaw lock devices, more than ample skill to have achieved the present invention, but only if the concepts and their combination had been conceived;

(h) Substantially all of the operational characteristics and advantages of details of the present invention, when considered separately from one another and when considered separately from the present invention's details and non-technical accomplishment of the details, are within the skill of persons of various arts, but only when considered away from the integrated and novel combination of concepts which by their cooperative combination achieves this advantageous invention;

(i) The details of the present invention, when considered solely from the standpoint of construction, are exceedingly simple; and the matter of simplicity of construction has long been recognized as indicative of inventive creativity;

(j) Similarly, and a long-recognized indication of inventiveness of a novel combination, is the realistic principle that a person of ordinary skill in the art, as illustrated with respect to the claimed combination as differing in the stated respects from the prior art both as to construction and concept, is presumed to be the one who thinks along the line of conventional wisdom in the art and is not one who undertakes to innovate; and (k) Advantageous mandible jaw locks are of an extremely useful need, a need which is often crucial and even life-saying, in a great variety of emergency and non-emergency situations.

Accordingly, although the prior art has had capability and motivation, amply sufficient to presumably give incentive to the development of a novel and practical device according to the present invention, the fact remains that this invention awaited the creativity and inventive discovery of the present inventor. In spite of ample motivation and capability shown by the many illustrations herein, the prior art did not suggest this invention.

V. PRIOR ART AS PARTICULAR INSTANCES OF FAILURE TO PROVIDE THIS NOVEL DEVICE

In view of the industry motives and capabilities, it may be difficult to realize that the prior art has not projected itself to the combination purpose and achievement of the present invention, even though the need and use of mandible jaw locks for dentists and other medical professionals is a widespread daily and quite universal factor, and the medical appliance industry is quite commercial and competitive. Further, mandible locks users surely include an uncountable multitude of inventors and other persons, at least of sufficient experience, skill, etc., that the present invention would have been desired and attempted, and perhaps achieved, long ago, but only if its factors and combination-nature had been obvious.

The consideration of a nature of the present inventive concepts will be helped by a consideration of the prior art cited.

As to jaw-locking as a function or capability, nothing is here asserted to be novel; and, in contrast, the concepts of the present invention provide the building upon the principal nature and function of earlier jaw lock devices and their concepts, rather than any modification of the lock device function itself/themselves.

VI. SUMMARY OF THE PRIOR ART'S LACK OF SUGGESTIONS OF THE CONCEPTS OF THE INVENTION'S COMBINATION

In spite of all such factors of the prior art, the problem here solved awaited this inventor's consideration, ideas, and creativity. More particularly as to the novelty here of the invention as considered as a whole, the resume of the prior art uses and needs helps show its contrast to the present concepts, and emphasizes the advantages, novelty, and the inventive significance of the present concepts as are here shown, particularly as to utility and convenience of use as detailed herein, as to apparatus and as to a procedure.

Moreover, prior art articles known to this inventor, which could possibly be adapted for this duty, fail to show or suggest the details of the present concepts as a combination; and a realistic consideration of the prior art's differences from the present concepts of the overall combination may more aptly be described as teaching away from the present invention's concepts, in contrast to suggesting them, even as to a hindsight attempt to perceive suggestions from a backward look into the prior art, especially since the prior art has long had much motivation as to details of the present invention and as to its provisions.

And the existence of such prior art knowledge and related articles embodying such various features is not only conceded, it is emphasized; for as to the novelty here of the combination, of the invention as considered as a whole, a contrast to the prior art helps also to remind both the variety of the various prior art articles and needed attempts of improvement, and the advantages and the inventive significance of the present concepts. Thus, as shown herein as a contrast to all the prior art, the inventive significance of the present concepts as a combination is emphasized, and the nature of the concepts and their results can perhaps be easier seen as an invention.

Although varieties of prior art are conceded, and ample motivation is shown, and full capability in the prior art is conceded, no prior art shows or suggests details of the overall combination of the present invention, as is the proper and accepted way of considering the inventiveness nature of the concepts.

That is, although the prior art may show an approach to the overall invention, it is determinatively significant that none of the prior art shows the novel and advantageous concepts in combination, which provides the merits of this invention, even though certain details are shown separately from this accomplishment as a combination.

And the prior art's lack of an invention of a handy and novel mandible lock tool achieving the convenience, ease of lock installation, ease of use, simplicity of use, and other advantages of the present invention, which are goals only approached by the prior art, must be recognized as being a long-felt need now realized.

Accordingly, the various concepts and components are conceded and emphasized to have been widely known in the prior art as to various devices; nevertheless, the prior art not having had the particular combination of concepts and details as here presented and shown in novel combination different from the prior art and its suggestions, even only a fair amount of realistic humility to avoid consideration of this invention improperly by hindsight, requires the concepts and achievements here to be realistically viewed as a novel combination, inventive in nature. And especially is this a realistic consideration when viewed from the position of a person of ordinary skill in this art at the time of this invention, and without trying to reconstruct this invention from the prior art without use of hindsight toward particulars not suggested by the prior art.

VII. BRIEF DESCRIPTION OF THE DRAWINGS

The above description of the novel and advantageous invention is of somewhat introductory and generalized form. More particular details, concepts, and features are set forth in the following and more detailed description of an illustrative embodiment, taken in conjunction with the accompanying Drawings, which are of somewhat schematic and diagrammatic nature for showing the inventive concepts; and in the Drawings:

FIG. 1 is a isometric pictorial view of a mandible lock device according to the present invention, the view pictured on the paper in about the same tilted orientation as shown in FIG. 6, i.e., the device is illustrated with the manual support beams in the foreground, and tilted as in FIG. 6, with the force lugs in the background, with only one of them showing in this view, the other force lug being mostly hidden;

In FIGS. 2 and 3 the device is tilted such that the support beam members are shown in almost full length; whereas in FIGS. 4 and 5 the device is tilted such that the support beams are oriented such that their axes are almost in "point view", the beams in FIGS. 4 and 5 thus appearing much shorter than as they are seen in FIGS. 2 and 3;

FIG. 2 is an elevation view of the mandible lock device of FIG. 1, showing the teeth-engaging force lugs in an intermediate position as held by the rachet lock feature of the device, FIG. 2 being an elevation view of the overall device as would be seen from a position interiorly of the patient's mouth, i.e., with the force lugs in the foreground and the support beams in the background, the view in FIG. 2 shown as taken outwardly, looking sideways of the person, looking toward the side of the person's mouth;

Figure 4:
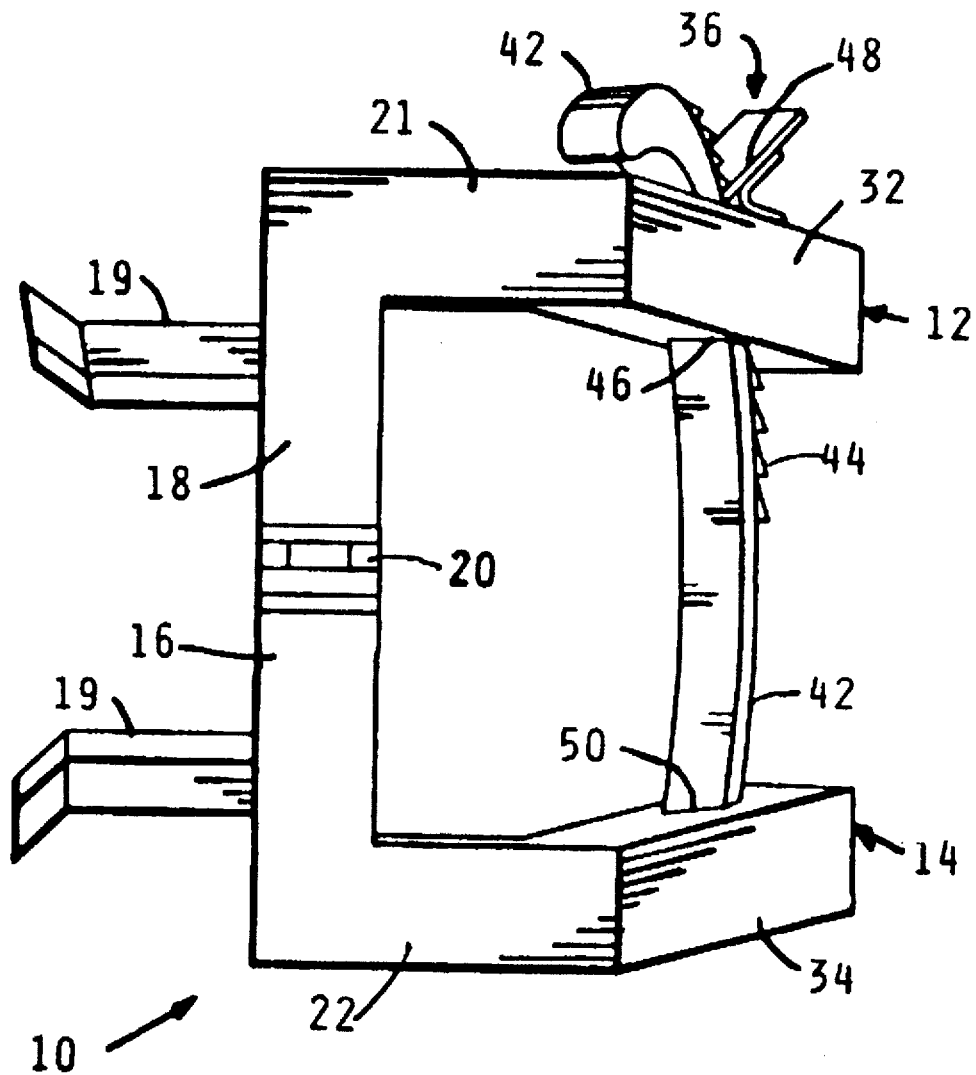
FIG. 4 is a pictorial isometric view of the device as would be seen from a viewpoint exteriorly of the patient's mouth, looking inwardly, with the lug holding beams being held in an intermediate position as in FIG. 2 by the rachet teeth shown in all views.
Figure 5:
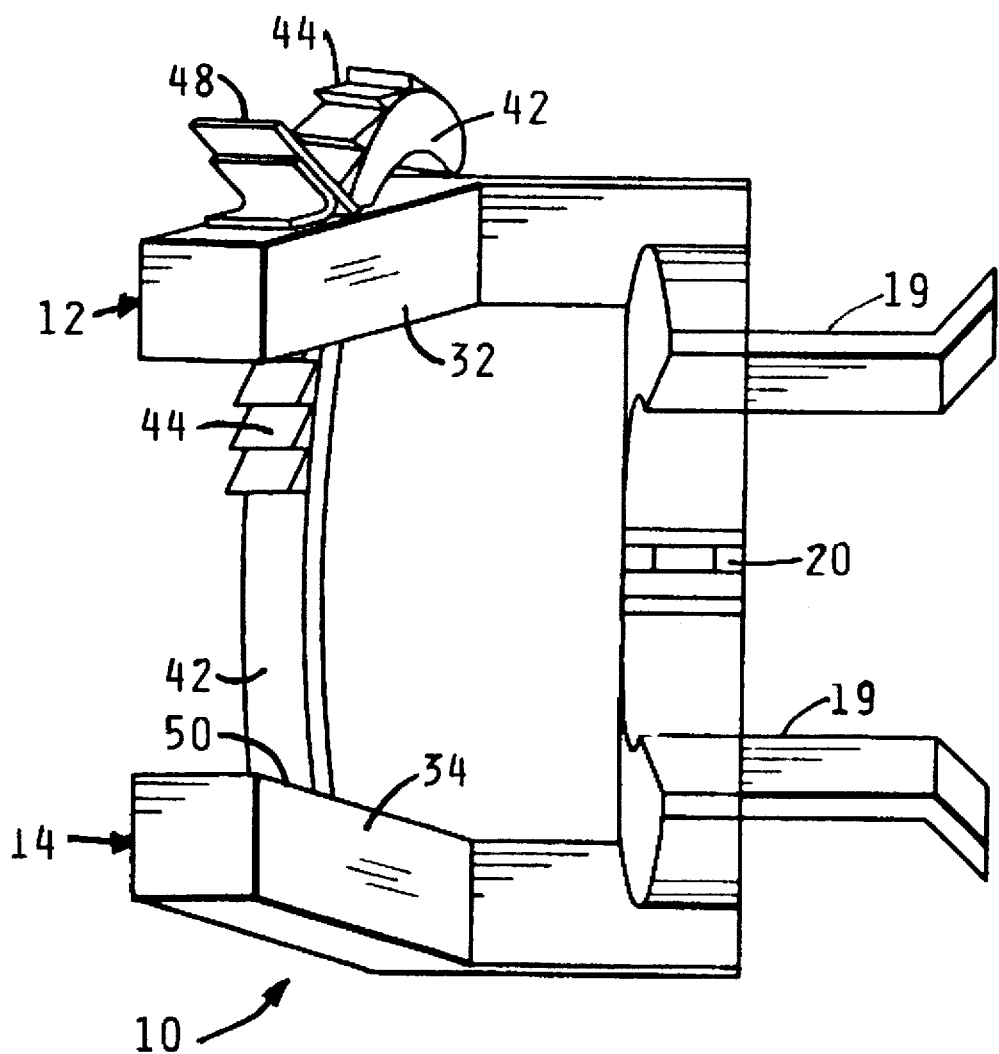
Figure 6:
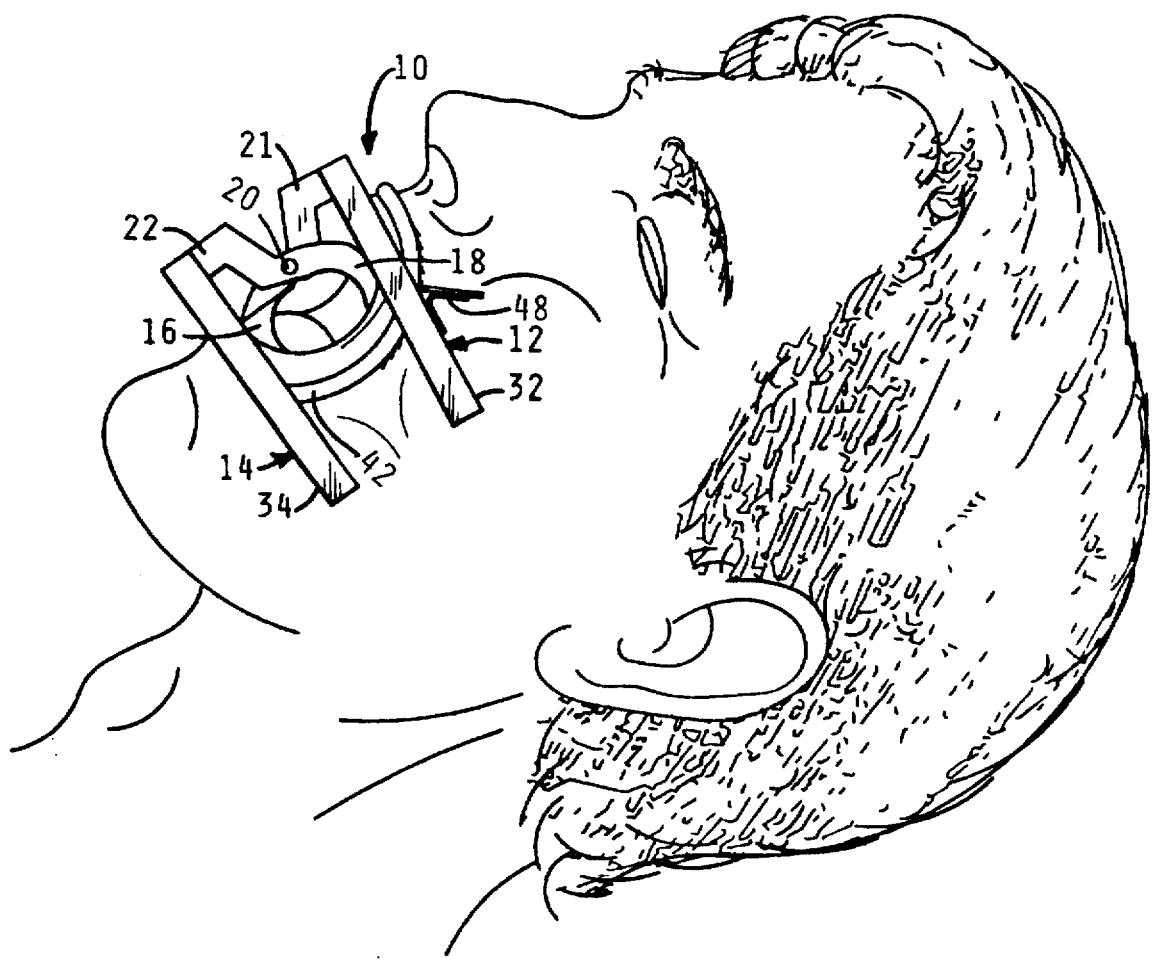

FIG. 5 is a pictorial isometric view similar to FIG. 4, but taken from a viewpoint inside the patient's mouth, looking outwardly; and FIG. 6 is a view illustrating the use of the device, the tooth-engaging components being generally hidden within the patient's mouth but with a support beams being in the foreground as the patient is viewed, the patient's head being shown in a generally body-prone position, and with the mandible lock device shown correspondingly in a tilted or angle position as 90° from the angled position of the patient's head.

VIII. SUMMARIZED LISTING OF COMPONENTS 10 device as a whole
11a mandible (lower) teeth set
11b jaw (upper) teeth set
12 upper main beam
14 lower main beam
16 inner end of 12
18 inner end of 14
19 each force lug
20 pivot
21 outer end of 12
22 outer end of 14
32 retroflex portion of 21,12

34 retroflex portion of 22,14
36 latch feature
42 monitor beam of 36
44 ratchet teeth on 42
46 opening in 12,32 for 42
48 ratchet follower of 44,36
50 connection of 42 to 14,34

IX. DETAILED DESCRIPTION OF PREFERRED EMBODIMENT

Figure 1:
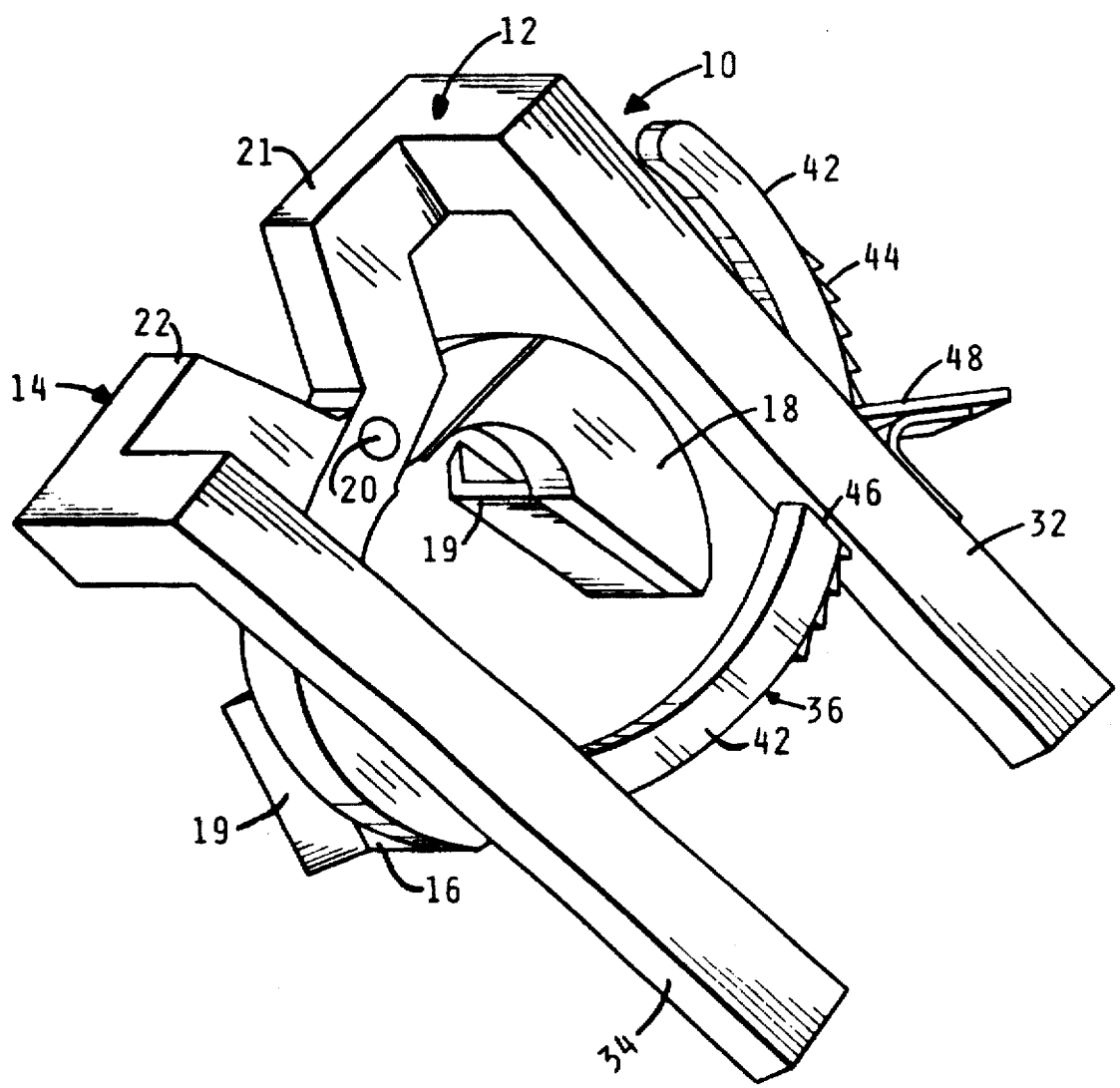
Figure 2:
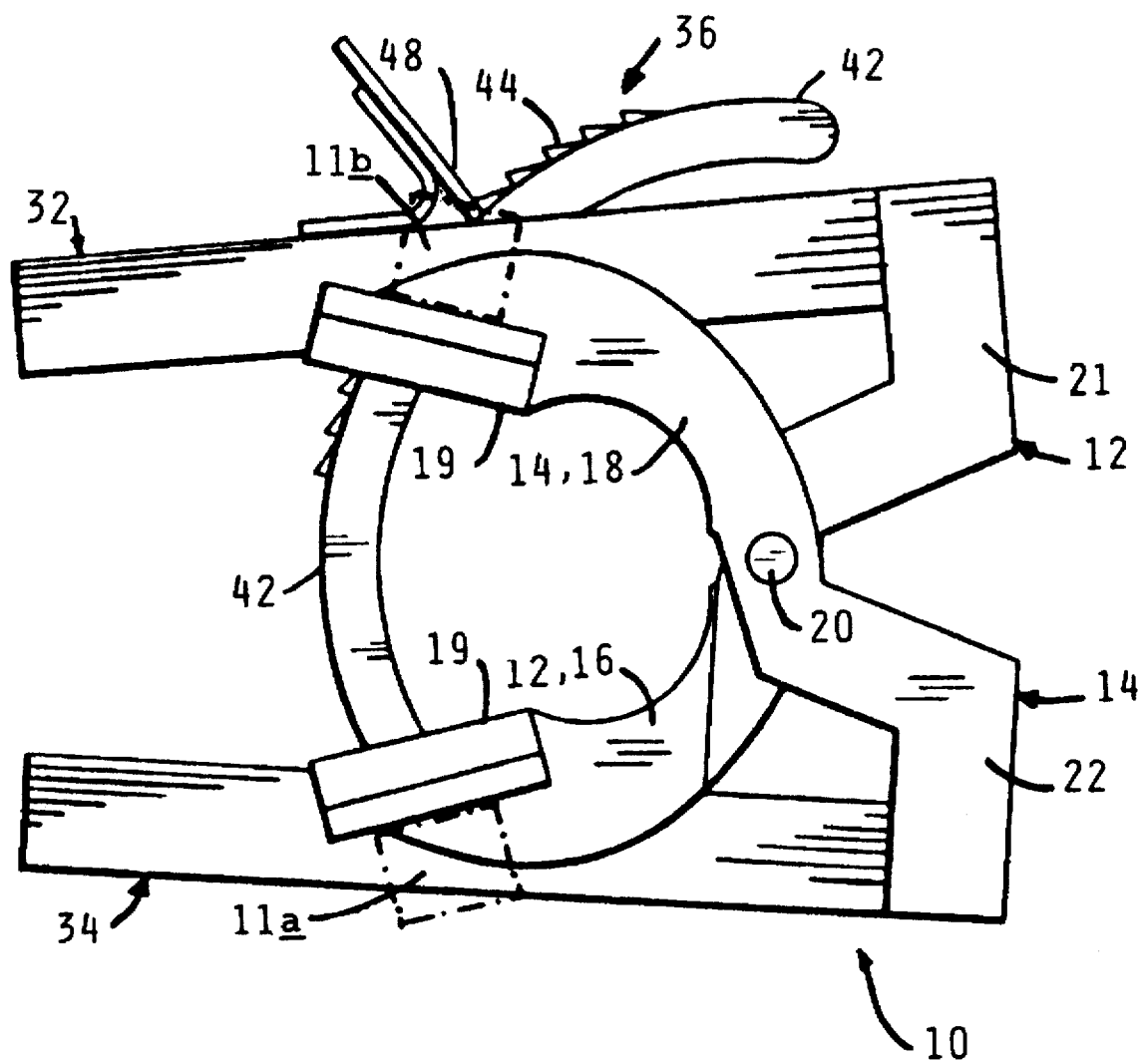
Figure 3:
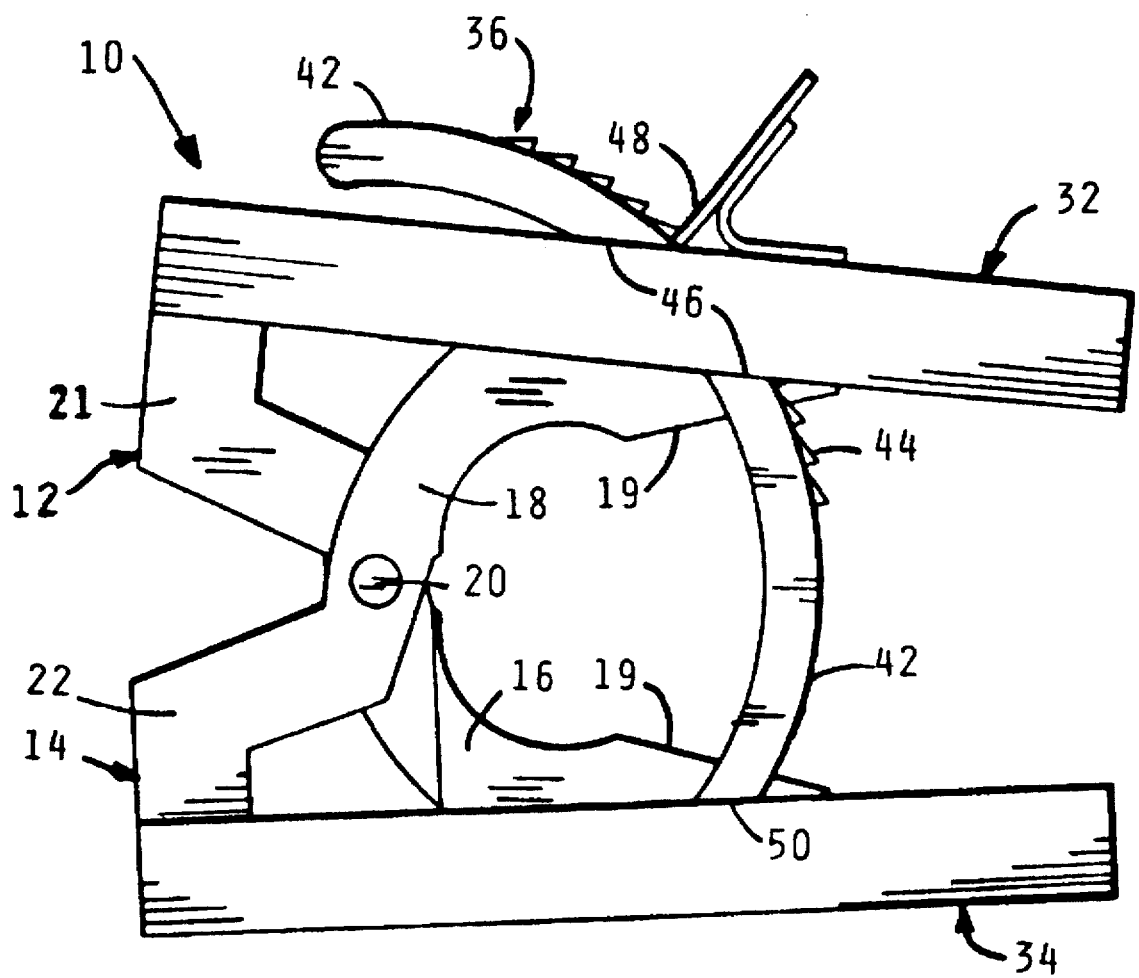
FIG. 3 is an elevation view of the device similar to the view shown in FIG. 2, but shown as taken from a viewpoint exteriorly of the patient's mouth, the view in FIG. 3 shown as taken from the side of the person's mouth.

As shown in the Drawings, the novel invention here presented provides a novel and advantageous jaw-lock device 10, more particularly a locking device for holding an "open position" of a person's mandible jaw bone and its mandible teeth set 11a relative to the person's skull and the teeth set 11b carried downwardly extending from the skull. (The teeth sets 11a and 11b are indicated diagrammatically in FIG. 2.)

In certain basic characteristics the device 10 is comparable to a mandible lock device of the Molt "Mouth Gag" type of the prior art, particularly in basic formation; but as herein specified the present invention builds upon the basic Molt construction and its kinematics, providing advantages of operability and manipulation by novel means which correspondingly avoids disadvantages of the Molt type Mouth Gags.

As with the Mouth Gag device of the Molt type prior art, the locking device 10 of the present invention basically comprises a pivotally interconnected pair of support beam members 12/14; and each of the support beam members 12/14 carries as its inner end (16 and 18 respectively), a force lug 19. ("Inner" is used here descriptively to indicate the portion of the device 10 which, in use, is placed inwardly of the person's mouth.) The force lugs 19 lie generally opposite one another, and are movable by a squeezing movement of their respective support beams 12/14 to impose a mandible-open force acting between the person's mandible teeth 11a and the skull teeth 11b.

The support beam members 12/14 are shown as pivotally connected by pivot 20 intermediate their inner ends 16/18 and outer ends 21/22; and the placement of the support beam members 12/14 in the person's mouth, and the functioning of the pivot 20, is such that the support beam members 12/14 lie in a generally vertical plane, and move in that plane in the manipulative step by which the force lugs 19 are caused to impose the lock-open force against the person's teeth sets, with both support beam members 12/14 (and their force lugs 19) being vertically disposed and on the same side of the person's mouth.

Quite significantly different from the prior art, the outer ends 21/22 of the support beam members 12/14 are provided as retroflex members 32/34 (respectively of beams 12/14) which, when the device is operatively inserted into the person's mouth, extend generally rearwardly along the exterior portion of the person's respective cheek.

Preferably the retroflex portions 32/34 are provided as integral extensions of the outer end portions 21/22 of the support beam members 12/14.

The retroflex portions 32/34 provide easily graspable handle-like members which handily provide for the manipulation of locking and unlocking the force lugs 19 against the person's teeth sets, but are advantageously out of the way of all access to the person's mouth.

The locking feature 36 provides that a squeezing manipulation of the support beam members 12/14 forces the force lugs 19 relatively vertically apart with respect to one another; and the medical professional accordingly has to impart a forceful movement to the support beam members 12/14 and more specifically against their retroflex portions 32/34, such that the force lugs 19 are firmly forced vertically apart, against the respective teeth sets 11a and 11b locking the mandible jaw in "open" position.

Analogous to prior art, the latch-type locking means 36 permits the relative pivoting of members 12/14 about pivot 26, but to firmly hold the beams 12/14 in the mouth-clamping position when manipulated such that the lugs 19 forcefully engage the teeth sets indicated diagrammatically as 11a and 11b.

As shown, the locking means 36 comprises a monitor beam 42 carried by one of the beams 12 or 14 (here beam 14), concentric about the pivot pin 20 and carrying ratchet teeth 44 which are latchingly engageable by spring-like ratchet follower member 48 carried on the other (here 12) of the beams 12 or 14. The connection of 42 to 14,34 is indicated at 50.

The nature of the follower member 48 is such that it yields resiliently to achieve tooth-clamping force operative between the beams 12/14, but follower 48 is stiff enough that it maintains a set position of beams 12/14 until the medical professional desires to release the latching engagement for loosening and withdrawal of the device 10 from the patient's mouth.

It will be noted that the monitor beam 42 passes through an opening 46 in one of the support beams 12/14 to which it is not attached, thus minimizing the bulk of the handle beams 12/14 by providing them to generally lie in a common plane.

X. SUMMARY OF THE ADVANTAGES

The present invention as detailed herein has advantages in both concept and in component parts and features; for in contrast to other articles known to the inventor as to the prior art mentioned, the invention provides advantageous features which should be considered, both as to their individual benefit, and to whatever may be considered to be also their synergistic benefit toward the invention as a whole. Such features include:

(a) Easy to use, with advantages of both handiness and avoidance of obstruction of access;

(b) Use is easy to learn;

(c) Advantageous mandible jaw locking is provided without the disadvantage of prior art devices;

(d) Economical of formation; and (e) Avoids the cost and storage problem of having to own a plurality of jaw locking devices.

XI. CONCLUSION AS TO INVENTIVE COMBINATION

It is thus seen that a combination type apparatus constructed and used according to the combination of inventive concepts and details herein set forth, provides novel concepts of a desirable and usefully advantageous article and procedure, yielding advantages which are and which provide special and particular advantages when used as herein set forth.

In summary as to the nature of the overall device's advantageous concepts, their novelty and inventive nature is shown by novel features of concept and construction shown here in advantageous combination and by the novel concepts hereof not only being different from all the prior art known, even though pivoted-handle clamps and other tools even jaw-lock tools of various types have been known and been used for scores of years, but because the achievement is not what is or has been suggested to those of ordinary skill in the art, especially realistically considering this as a novel combination comprising components which individually are similar in nature to what is well known to most all persons, surely including most of the many makers and users of jaw-lock devices and accessories for a large number of years, throughout the entire world. No prior art component or element has even suggested the modifications of any other prior art to achieve the particulars of the novel concepts of the overall combination here achieved, with the special advantages which the overall combination article provides; and this lack of suggestion by any prior art has been in spite of the long worldwide use of various types of jaw-lock devices and such appliances.

The differences of concept and construction as specified herein yield advantages over the prior art; and the lack of this invention by the prior art, as a prior art combination, has been in spite of this invention's apparent simplicity of the construction once the concepts have been conceived, in spite of the advantages it would have given, and in spite of the availability of all the materials, to all persons of the entire world, and the invention's non-technical and openly-visible nature.

Quite certainly this particular combination of prior art details as here presented in this overall combination has not been suggested by the prior art, this achievement in its particular details and utility being a substantial and advantageous departure from prior art, even though the prior art has had similar components for numbers of years. And particularly is the overall difference from the prior art significant when the non-obviousness is viewed by a consideration of the subject matter of this overall device as a whole, as a combination integrally incorporating features different in their combination from the prior art, in contrast to merely separate details themselves, and further in view of the prior art not achieving particular advantages here achieved by this combination.

Accordingly, it will thus be seen from the foregoing description of the invention according to this illustrative embodiment, considered with the accompanying drawings, that the present invention provides new and useful concepts of a novel and advantageous article and procedure, possessing and yielding desired advantages and characteristics in formation and use, and accomplishing the intended objects, including those hereinbefore pointed out and others which are inherent in the invention.

Modifications and variations may be effected without departing from the scope of the novel concepts of the invention; accordingly, the invention is not limited to the specific embodiment or form or arrangement of parts herein described or shown.

E.g., although each of the beam-pairs is shown as integrally providing the retroflex portion, and is a desirable embodiment, the concepts are not limited to integralness of that nature. And although the device was first contemplated to the inventor as being for use with human patients, the concepts are not limited in that respect.

Further, generally throughout the words "teeth" and "teeth set" are to be interpreted in their broad sense as operatively considered as objects of the jaw-locking force procedure; that is, their use is to broadly indicate the direct or indirect one or more tooth regions through which the jaw-locking force is transmitted, thus even including the socket region or regions transmissive of such force if the respective tooth or teeth have been lost or extracted.

I claim:

1. In a mandible lock device for holding an open position of a person's mandible bone and its mandible teeth set relative to the person's skull and its skull teeth set, the device comprising a cooperating pair of force lugs for imposing a mandible-open force acting between the person's mandible teeth set and skull teeth set, and a pair of support beam members, each of which support beam members carries one of the force lugs, each of the support beam members having an inner end and an outer end, the inner end of each respective support beam member carrying one of the force lugs, the support beam members being pivotally interconnected intermediate their inner ends and outer ends, and means to lock the beam members in a relative position such that the force lugs apply oppositely-directed force to bias and hold the mandible bone to be in open position, the support beam members and their force lugs being such that the device may be operatively inserted into the person's mouth with the force lugs generally opposite to one another, and on the same side of the person's mouth, for such a device, the improvement of an extension arm extending laterally of each support beam member at the outer end thereof, and having a retroflex portion which, when the device is operatively inserted into the person's mouth, extends generally rearwardly along the exterior portion of the person's respective cheek.

2. The invention set forth in claim 1, in which both support beam members and their respective retroflex extension arms are formed each as a part of an integral member.

3. The invention set forth in claim 1, in which the lock means includes a monitor member carried by one of the support beam members, and which is releasably fixable to the other support beam member, and the monitor member movably passes through a recess provided in the said other support beam member, accommodating an end portion of the monitor member which is opposite to the portion of the monitor member carried by the said one of the said support beam members.

4. The invention set forth in claim 1, in which the extension arms' retroflex portion extends rearwardly such that when the user applies a beam members-squeezing force to the beam members' retroflex portions it will act at a location on the side of the pivotal connection which has the force lug of each extension arm.

5. The invention as set forth in claim 4, in which both support beam members and their respective retroflex extension arms are formed each as a part of an integral member.

6. The invention as set forth in claim 4, in which the lock means includes a monitor member carried by one of the support beam members, and which is releasably fixable to the other support beam member, and the monitor member movably passes through a recess provided in the said other support beam member, accommodating an end portion of the monitor member which is opposite to the portion of the monitor member carried by the said one of the said support beam members.

* * * * *